United States Patent [19]

Strauss et al.

[11] Patent Number: 5,800,408

[45] Date of Patent: Sep. 1, 1998

[54] INFUSION DEVICE FOR DISTRIBUTING INFUSATE ALONG AN ELONGATED INFUSION SEGMENT

[75] Inventors: Jonathan H. Strauss, Laguna Niguel; Blair D. Walker, Long Beach, both of Calif.

[73] Assignee: Micro Therapeutics, Inc., San Clemente, Calif.

[21] Appl. No.: 746,302

[22] Filed: Nov. 8, 1996

[51] Int. Cl.$^6$ .................................................. A61M 25/00
[52] U.S. Cl. .................. 604/264; 604/48; 604/93; 604/246; 604/280; 137/876; 137/625.47
[58] Field of Search ............................. 604/27, 28, 48, 604/52, 53, 93, 49, 30, 32, 19, 264, 270, 280–284, 266, 194, 246, 248; 137/876, 874, 625.47; 128/656–658, 772

[56] References Cited

U.S. PATENT DOCUMENTS

| | | |
|---|---|---|
| 1,973,845 | 9/1934 | Chenoweth . |
| 3,316,937 | 5/1967 | Friedman et al. . |
| 3,384,089 | 5/1968 | Shriner .................................. 604/280 |
| 3,426,544 | 2/1969 | Curtis ........................................ 61/13 |
| 3,601,320 | 8/1971 | Du Plessis ............................ 239/542 |
| 3,698,195 | 10/1972 | Chapin ................................ 239/542 |
| 3,759,295 | 9/1973 | Dence .............................. 137/625.47 |
| 3,774,604 | 11/1973 | Danielsson ......................... 128/214.4 |
| 3,780,736 | 12/1973 | Chen ..................................... 128/231 |
| 4,187,882 | 2/1980 | Watson ............................ 137/625.47 |
| 4,318,402 | 3/1982 | Vaillencourt .......................... 604/280 |
| 4,717,379 | 1/1988 | Ekholmer .............................. 604/280 |
| 4,904,245 | 2/1990 | Chen et al. ............................. 604/248 |
| 4,915,133 | 4/1990 | Harrison ........................... 137/625.47 |
| 4,927,418 | 5/1990 | Dake et al. ............................. 604/264 |
| 4,961,731 | 10/1990 | Bodicky et al. ....................... 604/264 |
| 4,967,797 | 11/1990 | Manska ............................. 137/625.47 |
| 4,968,307 | 11/1990 | Dake et al. ............................. 604/264 |
| 4,995,865 | 2/1991 | Gahara et al. ........................... 604/43 |
| 5,004,455 | 4/1991 | Greenwood et al. .................... 604/43 |
| 5,010,924 | 4/1991 | Jenn ................................. 137/625.47 |
| 5,021,044 | 6/1991 | Sharkawy ................................ 604/53 |
| 5,085,635 | 2/1992 | Cragg ...................................... 604/96 |
| 5,135,026 | 8/1992 | Manska ................................. 137/555 |
| 5,203,769 | 4/1993 | Clement et al. .......................... 604/32 |
| 5,207,641 | 5/1993 | Allton ....................................... 604/32 |
| 5,224,929 | 7/1993 | Remiszewski .......................... 604/30 |
| 5,250,034 | 10/1993 | Appling et al. ........................ 604/164 |
| 5,251,663 | 10/1993 | Christianson et al. ................. 137/876 |
| 5,295,962 | 3/1994 | Crocker et al. ........................ 604/101 |
| 5,320,599 | 6/1994 | Griep et al. ............................. 604/35 |
| 5,329,921 | 7/1994 | Socaris et al. ..................... 128/207.14 |
| 5,370,610 | 12/1994 | Reynolds ................................ 604/43 |
| 5,380,307 | 1/1995 | Chee et al. ............................ 604/264 |
| 5,425,723 | 6/1995 | Wang .................................... 604/280 |
| 5,443,453 | 8/1995 | Walker et al. ......................... 604/248 |
| 5,466,228 | 11/1995 | Evans .................................... 604/248 |
| 5,617,815 | 4/1997 | Spies et al. ............................. 123/41.1 |
| 5,626,564 | 5/1997 | Zhan et al. ............................ 604/164 |
| 5,674,193 | 10/1997 | Hayes ..................................... 604/28 |

*Primary Examiner*—Corrine M. McDermott
*Assistant Examiner*—Cris L. Rodriguez
*Attorney, Agent, or Firm*—Joseph F. Breimayer

[57] ABSTRACT

An infusion device for use in delivering an infusate from an elongated infusion segment along an elongated section of a body vessel with either a relatively symmetric infusate distribution profile or asymmetric infusate distribution profile that concentrates infusate delivery proximally or distally along the infusion segment. The infusion segment is formed with an infusate distribution manifold for delivering infusate through a plurality of side wall exit ports in the elongated infusion segment having proximal and distal manifold end openings to which infusate is delivered in equal amounts to effect the relatively uniform infusate distribution profile or in relative proportions to effect the asymmetric infusate distribution profile. In differing embodiments, the infusate delivery is either fixed or may be adjusted by a proximal adjustable valve mechanism. The infusate is delivered through separate first and second infusion lumens to the distal and proximal manifold end openings, respectively, which preferably comprise inner and annular lumens formed by inner and outer coaxial tubes such that the distal section of the annular lumen forms the manifold.

37 Claims, 8 Drawing Sheets

INFUSION DEVICE FOR DISTRIBUTING INFUSATE ALONG AN ELONGATED INFUSION SEGMENT

CROSS-REFERENCE TO RELATED APPLICATION

Reference is hereby made to commonly assigned, co-pending U.S. Pat. application Ser. No. 08/326,609 filed Oct. 20, 1994, for INFUSION DEVICE WITH PRE-FORMED SHAPE in the names of George B. Wallace, et al.

1. Field of the Invention

The present invention relates to infusion catheters for use in delivering a therapeutic or diagnostic agent to a body vessel, and particularly to such a catheter having an elongated infusion segment and a mechanism for delivering the therapeutic agent to an elongated section of a blood vessel with an adjustable profile.

2. Description of the background Art

A wide variety of infusion catheters, including infusion wires that also function as guide wires for introducing larger diameter catheters, are known in the art for infusing an infusate, e.g. a therapeutic agent or drug or a diagnostic agent, into a body vessel. One use of infusion catheters is to deliver a thrombolytic agent, e.g., streptokinase, urokinase, TPA or the like, to a section of a blood vessel that is blocked by a soft obstruction, e.g. a thrombus or blood clot. The acute symptoms of blockage of a vein at a venous valve or a partially sclerosed and narrowed artery may be instigated by the presence of a soft obstruction or blood clot that is soft and jelly-like in consistency. Such blood clots may form for a variety of reasons in the vascular system and be released and flow until they block a partially occluded section of the blood vessel. When this clot blocks a vessel in the leg, for example, the resultant pain or loss of circulation requires its removal or dissolution.

Such soft obstructions are readily penetrated but reform after the penetrating object is removed. To effect the initial opening of a soft obstruction, thrombolytic drugs or clot dissolving agents may be applied through an infusion catheter inserted into the clot to encourage the dissolution of the clot. For example, the infusion catheter disclosed in U.S. Pat. No. 5,085,635 is proposed to be introduced over a guide wire previously advanced through the soft obstruction and be used for infusion of thrombolytic drugs (as well as diagnostic agents, in other procedures) out side wall exit ports into contact with the soft obstruction. In the simplest infusion catheters, one or more side exit port(s)and/or an end opening are provided in a distal segment of the catheter body that are in communication with an infusion lumen extending the length of the catheter body to the proximal end thereof and through which the thrombolytic agent is infused from a pressurized source at the proximal end.

In certain instances, the blood clot may extend over an elongated section of the blood vessel up to 100 cm long in severe cases, e.g., the a clot in the peripheral venous system. It is very desirable in such cases to distribute the thrombolytic agent over as much of the length of the obstruction as can be accessed. Currently, commercially available infusion wires have infusion segment lengths of up to 12 cm and infusion catheters have infusion lengths of up to about 30 cm in length. In order to access small vessels, the infusion catheter outer diameter, and consequently, the infusion lumen(s) for delivering the agent and possibly accommodating a guide wire (also referred to as a core wire in the case of an infusion wire) are necessarily small. The flow rate and volume of the infused agent is therefore dictated by a number of factors including the infusion lumen size, the number and sizes of the exit ports and/or end opening, and the fluid pressure that may be safely used. The distribution of the agent is typically non-uniform or uniform over only a relatively short distance. One reason for this is that when a multitude of side wall exit ports are provided in communication with a single infusion lumen, the pressure gradient falls off distally as infusate escapes the more proximal ports. The attenuation in the distribution of infusate is most severe at the distal end of a relatively long infusion segment having multiple infusion side exit ports distributed circumferentially about the periphery of the side wall.

In the context of treating elongated blood clots, the non-uniform distribution can be a problem because the clot is lysed incompletely or inconsistently along its length, leaving remnants that have to be dealt with. This can occur particularly in blood vessels demonstrating low blood flow rate.

A number of approaches have been taken to address the non-uniform distribution of the infusate in infusion catheters, typically having a shorter infusion segment. In U.S. Pat. No. 5,425,723, a lengthy dissertation of the problems involved in providing a uniform distribution of infusate along the length of an elongated infusion segment is set forth. In general, the longer the flow path followed by a fluid under pressure in a lumen of constant diameter, the higher the resistance and the higher the pressure drop. Moreover, the resistance and pressure drop gradiant is proportional to the viscosity of the fluid and the cross-section area of the lumen. As viscosity increases and cross-section diminishes, the resistance to flow through a lumen or the exit port from the lumen increases. The lumen size of infusion catheters and infusion wires is dependent on the chosen outside diameter, acceptable construction and wall thickness to accomplish the positioning of the distal infusion segment, the number of lumens and the need to accommodate a guide wire or core wire in a lumen. These factors result in an infusion lumen of maximum cross-section for accommodating flow of the fluid infusate.

An early approach taken in a single lumen infusion catheter to counter the pressure drop and increased resistance to fluid flow was to progressively increase the number and/or size of side wall exit ports distally as incorporated into the infusion catheter shown in U.S. Pat. No. 5,021,044, for example. This approach presents design challenges in determining the optimum exit port size relationship and manufacturing challenges in controlling the exit port sizes. Moreover, using only a single lumen to deliver the fluid to the distal infusion segment increases the pressure loss due to flow resistance down the lumen proximal segment.

The use of a plurality, e.g. four, 90° displaced apart infusion lumens of equal cross-section area leading to single side wall exit ports displaced along the length of infusion catheter distal segment and at 90° to one another is disclosed in U.S. Pat. Nos. 4,927,418 and 4,968,307. While uniform distribution around the catheter exterior is alleged, this limited number of exit ports and the necessarily small infusion lumen cross-section severely limits the length of distribution in the infusion segment. Certainly, if the infusion segment is relatively short, it is likely that a relatively uniform amount of infusate can be delivered from each exit port over a given test period in an in vitro test environment. However, the differences in the resistance to fluid flow in the four lumens is magnified proportionally as the differences in lengths of the lumens increases in order to increase the infusion segment length. The differences in resistance leads to a higher flow rate from the proximal exit ports than from the more distal exit ports. Moreover, in clinical practice, one or more of the exit ports may be blocked against a vessel side wall, thereby limiting the amount of infusate infused in the body vessel both around the body of the catheter and distally and proximally. The purported performance advantage may be readily thwarted by a single blocked exit port.

A further approach employing a large number of side wall exit ports in the infusion segment is shown in the '723 patent employing a coaxially arranged inner tube having an inner infusate delivery and guide wire lumen and an outer tube defining an annular manifold between the inner and outer tubular member. The outer side wall exit ports are arranged about the distal infusion segment of the outer tube, and a further plurality of communication ports are formed in the side wall of the inner tube in order in a particular spaced relation to the outer exit ports. The relationship is designed to progressively shorten the pathways in the intermediate manifold between adjacent communication ports and side wall exit ports distally in the effort to make the distribution uniform along the length of the infusion catheter. This approach is relatively complex and inflexible once the design of the spacings is chosen. Moreover, since the communication ports are distributed along the length of the infusion segment, the annular separation of the outer and inner tube can collapse as the infusion segment is advanced in the blood vessel, and the communication ports may be blocked by the outer tube in the area of collapse.

It is desirable in certain instances to be able to tailor the distribution profile along the infusion segment length to achieve a particular concentration of liquid infusate along the infusion segment length. In the '418 patent, it is suggested that each of the four infusion lumens be provided with its own source of infusate and a mechanism for independently regulating the flow therethrough. Again, the small diameter of the individual infusion lumens and the single side wall exit port limit the utility of this suggested modification.

Despite these attempts to solve the problem there remains a need for an improved infusion device and method of use that increases the likelihood that a relatively symmetric distribution or a tailored distribution profile of a liquid infusate can be achieved over a length greater than 30 cm for infusion catheters and 12 cm for infusion wires in clinical use.

SUMMARY OF THE INVENTION

For convenience, the following terms are defined for use in the remaining description of the preferred embodiments and in the claims. The term "obstruction" embraces a blood clot or embolus or thrombus that is amenable to treatment in manner described hereafter. The term "infusate" is intended to embrace a variety of fluids used in medical practice for diagnostic purposes, e.g. delivering a radiopaque agent for observing the extent of such an obstruction or other defect along the length of the body vessel, or for treatment of a medical condition of a body vessel, particularly thrombolytic agents or other drugs or agents for penetrating, loosening or dissolving such obstructions, or other drugs for treating vessel defects. The term "infusion device" embraces infusion catheters, infusion wires and the like. The term "body lumen" includes blood vessel lumens containing such obstructions but also includes other blood vessel lumens or lumens of other body vessels or cavities where it is desired to deliver a selected infusate to treat other conditions or otherwise irrigate the lumen. It will be recognized that the present invention may have applications for infusing fluids in other types of body lumens for a variety of reasons where it is desired to deliver the infusate over a long infusion segment at a relatively constant or symmetric rate and volume achieving a relatively uniform distribution profile along the length, or, in certain embodiments described below, to tailor the distribution profile of the delivered infusate over the length of the infusion segment.

It is therefore a principal object of the present invention to provide an infusion device having an elongated infusion segment that delivers infusate having a relatively symmetric or tailorable distribution profile along the full length of the infusion segment.

It is yet another object of the present invention to provide such an infusion device for delivering thrombolytic agents for effecting the dissolution of or otherwise treating an elongated obstruction of a blood vessel in situ.

These and other objects of the invention are realized in an infusion device and method of use thereof for distributing an infusate in a relatively symmetric distribution profile along the length of an elongated distribution segment of the elongated infusion device comprising an elongated tubular body having an external side wall extending between a proximal end and a distal end adapted to be introduced intraluminally into a body lumen and having an infusion segment extending proximally from a distal infusion segment end and a proximal infusion segment end adapted to be intraluminally positioned within a corresponding length of the body lumen; an infusate distribution manifold formed within the elongated tubular body extending between the proximal and distal infusion segment ends and having proximal and distal distribution manifold end openings; a plurality of side wall exit ports extending through the side wall of the tubular body into the infusate distribution manifold and distributed along the infusion segment between the proximal and distal infusion segment ends, first delivery means for conducting infusate from the proximal end of the tubular body distally through the tubular body and through the distal manifold end opening at a first flow rate such that infusate flows distally through the first delivery means and proximally through the infusate distribution manifold and primarily through the side wall exit ports in the distal infusion section and into the body lumen; and second delivery means for conducting infusate from the proximal end of the tubular body distally through the tubular body and through the proximal manifold end opening at a second flow rate such that infusate flows distally through the infusate distribution manifold and primarily through the side wall exit ports in the proximal infusion section and into the body lumen.

Preferably, the first delivery means and second delivery means are formed of first and second infusion lumens having respective first and second proximal lumen end openings at the proximal end of the tubular body and distal lumen end openings in fluid communication with distal and proximal manifold ends, respectively. The infusate is delivered into the first and second proximal lumen end openings from a source of pressurized infusate.

In a preferred embodiment, the elongated tubular member further comprises an inner tube having an inner tube lumen and inner tube side wall and an outer tube having an outer tube lumen and outer tube side wall arranged in a co-axial arrangement wherein the inner tube is located within the outer tube lumen and an annular lumen is thereby formed between the inner tube side-wall and the outer tube side wall. The plurality of side wall exit ports are formed in the outer tube side wall in the distal infusion segment, and the infusate distribution manifold is formed of a distal section of the annular lumen extending through the length of the infusion segment having proximal and distal manifold end openings that are merely defined abutting sections of the annular lumen and infusate distribution manifold. The distal end of the outer tube is sealed to the distal end of the inner tube distally to the distal manifold end opening to inhibit distal leakage of infusate delivered into the infusate distribution manifold.

Therefore, the second infusion lumen is formed of the annular lumen extending proximally from the proximal manifold end to the second proximal lumen end opening. The infusate is then distributed distally therefrom within the infusion manifold, whereby the infusate is distributed primarily out the proximal portion of the plurality of side wall exit ports into the adjoining body lumen. The first infusion lumen is formed of the inner lumen extending from the first proximal lumen end opening distally within the second lumen and within the infusate distribution manifold to the tubular member distal end. At a point proximal to the tubular member distal end, one or more infusate transmission ports are formed in the inner tube side wall to deliver infusate from within the distal end of the inner lumen to the distal manifold end opening. The infusate is then distributed proximally therefrom within the infusion manifold, whereby the infusate is distributed out the distal portion of the plurality of side wall exit ports into the adjoining body lumen.

The delivery of the infusate into the proximal and distal manifold end openings may be effected in a fixed relation of flow rate and fluid pressure that affords an equal rate of flow therethrough so that the infusate distribution profile from the proximal and distal portions of the side wall exit ports are relatively equal or symmetric. The symmetric infusate distribution profile exhibits the greatest magnitude of flow rate and volume near the proximal and distal ends of the infusion segment, and the magnitude attenuates toward the mid-point of the infusion segment length.

In a variation of the first embodiment the relative fixed sizes of first and second orifices are sized in relation to first and second infusate flow resistances to establish a predetermined difference in the first and second flow rates, whereby infusate is delivered through the distal and proximal manifold end openings, respectively, at differing flow rates and fluid pressures for providing an asymmetric infusate distribution profile along the length of the infusion segment.

Alternatively, in accordance with a second embodiment of the invention, the infusion device further comprises an adjustable valve mechanism coupled to a source of infusate to receive the infusate and coupled to the first and second delivery means for proportionally diverting the infusate into the first and second delivery means in adjustable proportions. For example, a flow diverting valve is employed that may be selectively adjusted in use to define the first and second orifice sizes and the resulting flow rate of infusate through the first and second delivery means. In practice, the flow diverting valve may be incorporated into an infusion side port coupled to the proximal end of the tubular body in fluid communication with the first and second lumen proximal end openings.

In these embodiments, the inner lumen preferably defines a guide wire or core wire lumen for a removable guide wire or core wire. In an infusion catheter embodiment, the distal end of the inner tube is formed with a penetrable and re-sealable valve through which the guide wire extends. In use, the guide wire is first used to access the desired site in the body vessel. The infusion catheter is introduced to the desired site by advancing it over the guide wire in a manner well known in the art. Once in place, the guide wire is removed, and the distal end valve reseals to prevent loss of infusate from the first or inner lumen distal end. An infusion port body at the proximal end may include a re-sealable valve mechanism in the first infusion lumen for receiving the guide wire during the over the wire introduction of the infusion catheter and re-sealing upon removal of the guide wire from the inner lumen.

In other embodiments, where the first and second infusion lumens may be formed side by side, rather than co-axially, one of the lumens may be designated as a guide wire or core wire lumen, and in the former case, may be provided with a re-sealable valve to allow for the over the wire advancement to the desired site.

In these alternative embodiments, the infusion device may also be used as an infusion wire having a fixed or removable core wire that does not penetrate the distal end for adding column strength for advancement of the infusion wire through the obstruction. The fixed core wire extends within all or part of the inner lumen and is attached so that it cannot be removed. The removable core wire extends through the lumen and abuts the distal tip but can be removed when the infusion wire is positioned in order to increase the lumen cross-section area.

The improved infusion device and method of use of the present invention creases the likelihood that a relatively symmetric distribution or a tailored distribution profile of a liquid infusate can be achieved over a length greater than 30 cm for infusion catheters and 12 cm for infusion wires in clinical use. In the second embodiment, the length of the infusion segment can be advantageously shortened or lengthened or moved proximally or distally during patient treatment.

Advantageously, the invention may be used to remove elongated blood clots by the application of dissolving agent into the clot along the full length thereof. In the second embodiment, the distribution of the delivery of the dissolving agent may be initially optimized and adjusted during the delivery period as the clot dissolves. In both embodiments the infusion distribution profile may be made symmetric or assymetric.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figures 1, 2:
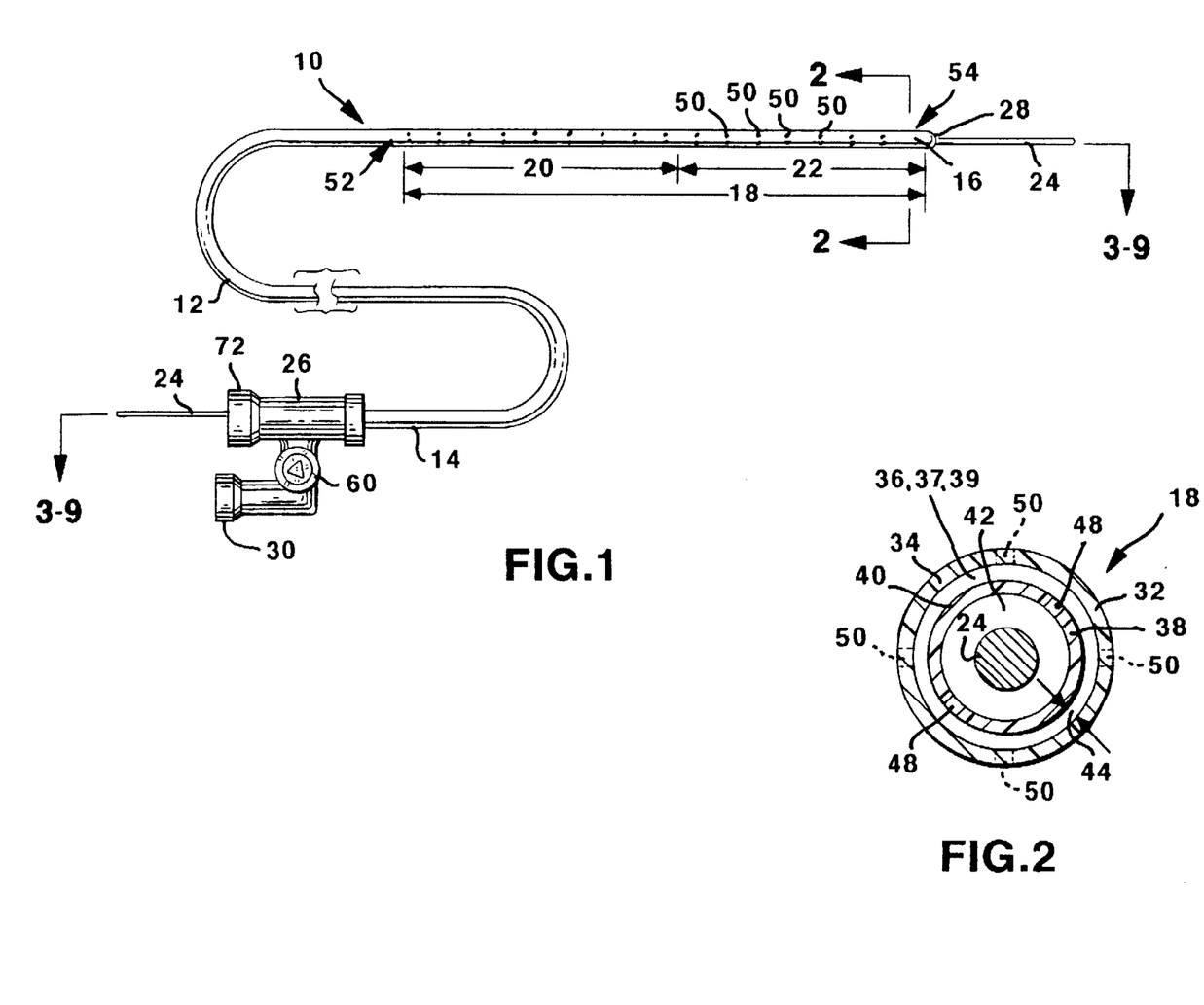
FIG. 1 is a plan view of the assembly of an infusion device according to the preferred embodiments of the present invention.
FIG. 2 is an end cross-section view of the distal end of the infusion segment of the infusion device of FIG. 1 depicting the inner tube, the outer tube and distal fluid communication ports for passing infusate from the inner tube lumen into the annular lumen between the inner and outer tubes.

Turning first to FIG. 1, it depicts the assembly of an infusion device 10 including a removable guide wire 24 extended through a guide wire lumen in accordance with the preferred embodiments of the present invention. The infusion device 10 is formed with an elongated tubular body 12 having an external side wall extending between a proximal tubular body end 14 and a distal tubular body end 16 adapted to be introduced intraluminally into a body or blood vessel lumen (not shown). A distal infusion segment 18, including an infusate distribution manifold as described below, extends proximally from a distal infusion segment end and distal manifold end opening essentially coextensive with distal end 16 and a proximal infusion segment end and proximal manifold end opening 52 adapted to be intraluminally positioned within a corresponding length of the body lumen. The distal infusion segment 18 is divided into a proximal infusion section 20 and a distal infusion section 22 for purposes of describing the infusate distribution profiles exhibited in FIGS. 3–9 and described below. Corresponding portions of the total number of side wall exit ports 50 are within the proximal and distal infusion sections 20 and 22. The side wall exit ports 50 are preferably of the same opening size and are preferably evenly distributed about the length and diameter of the tubular body 12 in the distal infusion segment 18, although variation in exit port size and distribution to achieve a preferred infusate distribution is contemplated for incorporation with the present invention.

The proximal end 14 of the tubular body 12 is received within a proximal fitting 26 having an axial end port 72 that preferably includes a conduit and re-sealable, proximal valve mechanism of a type well known in the art for receiving the guide wire 24 during the over the wire introduction of the tubular body 12 and for re-sealing upon retraction of the guide wire 24 proximally therethrough. With the guide wire 24 either present or withdrawn, the proximal valve mechanism prevents leakage of fluid infusate or body fluids from the proximal end 14 of tubular body 12. The infusate is introduced into the infusion lumens within tubular body 12 through a side port 30 as shown in FIGS. 3–9 and described below.

The distal end opening 28 of the tubular body 12 is also preferably provided with a penetrable and re-sealable valve of the type shown in U.S. Pat. No. 5,085,635 through which the guide wire 24 extends. In use, the guide wire 24 is first advanced transluminally to access the desired site in the body vessel. The infusion segment 18 of tubular body 12 is extended through the desired site by advancing it over the guide wire 24 in a manner well known in the art. Once in place, the guide wire 24 is retracted distally from fitting 26, and the distal end valve reseals to prevent loss of infusate from the guide wire lumen which is also used to deliver a portion of the infusate introduced into side port 30. The guide wire 24 is shown not necessarily to scale with respect to the tubular body 12.

In a first embodiment of the invention, the side port 30 is coupled to a source of infusate (not shown) and includes a first fixed size orifice for fluid infusate introduction through a first delivery means for distributing infusate from the proximal end 14 distally through the tubular body 12 and then proximally from the distal infusion segment end and distal manifold end opening 54 into the manifold and primarily out of the plurality of exit ports 50 in the distal section 22. Similarly, in the first embodiment, the infusate side port 30 includes a second fixed size orifice for fluid infusate introduction through a second delivery means for distributing infusate from the proximal end 14 distally through the tubular body 12 and then distally from the proximal infusion segment end and proximal manifold end opening 52 into the manifold and primarily out of the plurality of exit ports 50 in the proximal section 20.

In accordance with a second embodiment of the invention, the infusion device 10 further includes a variable valve mechanism coupled to a source of infusate (not shown) to receive the infusate and coupled to the first and second delivery means for diverting the infusate flow into the first and second delivery means in adjustable proportions. In this preferred embodiment, a flow diverting valve 60 is incorporated into side port 30 that defines first and second orifice sizes or flow rates and volumes by its adjustment and may be selectively adjusted in use to increase the flow of infusate into one of the first and second delivery means while reducing the flow of the infusate into the other of the first and second delivery means thereby altering the infusate distribution profile. It will be understood that FIG. 1 is intended to depict both embodiments, wherein the flow diverting valve 60 would not be present in the first embodiment, and to depict an infusion catheter or wire designed to be used with or without a guide wire 24.

The first and second delivery means between the infusate side port 30 and the distal and proximal ends of the infusion segment 18 may take a variety of forms. In the preferred embodiments depicted in the figures, the infusate is delivered into a single infusate distribution manifold within and extending the length of the infusion segment 18 in fluid communication with all of the side hole exit ports 50. A proximal manifold end opening 52 is defined at the proximal end of infusion segment 18 and a distal manifold end opening 54 is defined at the distal end of infusion segment 18 adjacent to distal end 16. The infusate distribution manifold is preferably of constant cross-section area through the length of distal infusion segment 18, and the proximal and distal manifold end openings 52 and 54 preferably have the same cross-section area so that equal portions by volume and flow rate of infusate can be delivered through them. In the first embodiment, the infusate is delivered through the first and second delivery means so that a fixed infusate distribution profile from the side hole exit ports 50 in the proximal and distal infusion sections 20 and 22 into the body vessel lumen is achieved. In the second embodiment, the proportions of infusate flowing into the proximal and distal manifold end openings 52 and 54 are variable through adjustment of the flow diverting valve 60 in infusate side port 30 so that the resulting infusate distribution profile can be tailored to concentrate flow volume proximally in proximal infusion section 20 or distally in distal infusion section 22.

Preferably, the infusate distribution manifold and first and second infusate delivery means are formed of a simple unitary tubular body structure defining first and second infusion lumens having respective first and second proximal lumen end openings at the proximal end 14 and first and second distal lumen end openings in fluid communication with the distal and proximal manifold end openings 54 and 52, respectively. Preferably, one of the infusion lumens (or a further lumen) is used as the guide wire 24 or core wire lumen in an infusion catheter or wire embodiment.

Turning to FIG. 2, it depicts the preferred embodiment of forming the first and second infusion lumens and the infusate distribution manifold viewed proximally at section lines 2—2 from the distal manifold end opening 54 with the guide wire 24 in place. Elongated tubular body 12 comprises an inner tube 38 having an inner tube side wall 40 enclosing the first infusion and guide wire lumen 42 and an outer tube 32 having an outer tube side wall 34 enclosing an annular lumen 36 having a separation 44 extending through the length of tubular body 12. This co-axial arrangement of the inner tube 38 located within the outer tube 32 forming the inner tube lumen 42 and annular lumen 36 extends the full length of the tubular body 12. The distal end of the outer tube 32 is sealed to the distal end of the inner tube 38 at distal tip 16 to enclose the annular lumen 36 and inhibit distal leakage of infusate delivered therein. The plurality of side wall exit ports 50 are formed in the outer tube side wall 34 in the infusion segment 18, and the infusate distribution manifold 37 is formed of the corresponding distal section of the annular lumen 36 extending through the length of the infusion segment 18. Consequently, the proximal section of annular lumen 36 extending from the proximal end opening at the proximal end 14 distally to the proximal manifold end opening 52 constitutes the second infusion lumen 39 in this preferred embodiment. The proximal manifold end opening 52 is simply the junction, without any flow restriction or barrier or the like, of the proximal and distal sections of the annular lumen 36 where the plurality of side wall exit ports 50 in outer tube 32 commence.

The first infusion and guide wire lumen 42 extends the full length of the tubular body 12 and preferably terminates in a guide wire penetrable and re-sealable distal valve in distal end opening 28. As shown in FIG. 2 and in the remaining FIGS. 3–9, a plurality of infusate transmission ports 48 are formed in the inner tube side wall 40 to deliver infusate from within the distal end of inner lumen 42 into the distal end of annular lumen 36 constituting the distal manifold end opening 54. As a general proposition, subject to exceptions as described below, it is an object of the first embodiment of the present invention to equalize the flow rate and volume of infusate entering the proximal and distal manifold end openings 52 and 54. Consequently, the cross-section area of the inner guide wire lumen 42 (without the guide wire 24 present) and the cross-section area of the annular lumen 36 are selected to offset differing flow resistance factors of length and side wall surface area that infusate contacts. They are selected so that the volume and pressure head of infusate delivered through the inner, first infusion lumen 42 to the infusate transmission ports 48 compensates for the greater delivery distance. The volume and pressure head of infusate delivered through the second infusion lumen 39 of the proximal portion of annular lumen 36 compensates for the flow resistance caused by fluid flow alongside both the outside wall of the inner tube 38 and the inside wall of the outer tube 32. The size and number of transmission ports 48 are selected to provide a total cross-section transmission port area, which in correlation to the pressure head and the cross-section areas of the annular and inner lumens 36 and 42, does not unduly restrict the transmission of infusate into the annular distal manifold end opening 54.

For example, in an infusion catheter embodiment, the diameter of inner lumen 42 may be on the order of about 0.040 inches, the thickness of inner tube side wall 40 may be about 0.004 inches and the annular lumen separation 44 may be about 0.006–0.010 inches. The cross-section area of the annular lumen 36 in the proximal section constituting the second infusion lumen 39 therefore exceeds the cross-section area of the inner, first infusion lumen 42 (in this example) to compensate for the greater flow resistance in the annular second infusion lumen 39, despite the greater length of the inner, first infusion lumen 42, due to the larger surface area of the spaced apart facing walls of the inner tube 38 and the outer tube 32 that the infusate contacts. The infusate transmission ports 48 may be about 0.012 inches in diameter, and about 16 infusate transmission ports 48 may be formed in the distal section of the inner tube side wall 40. The total cross-section area of the infusate transmission ports 48 therefore exceeds the cross-section area of the inner lumen 42 to avoid any infusate flow resistance therethrough.

Figure 3:
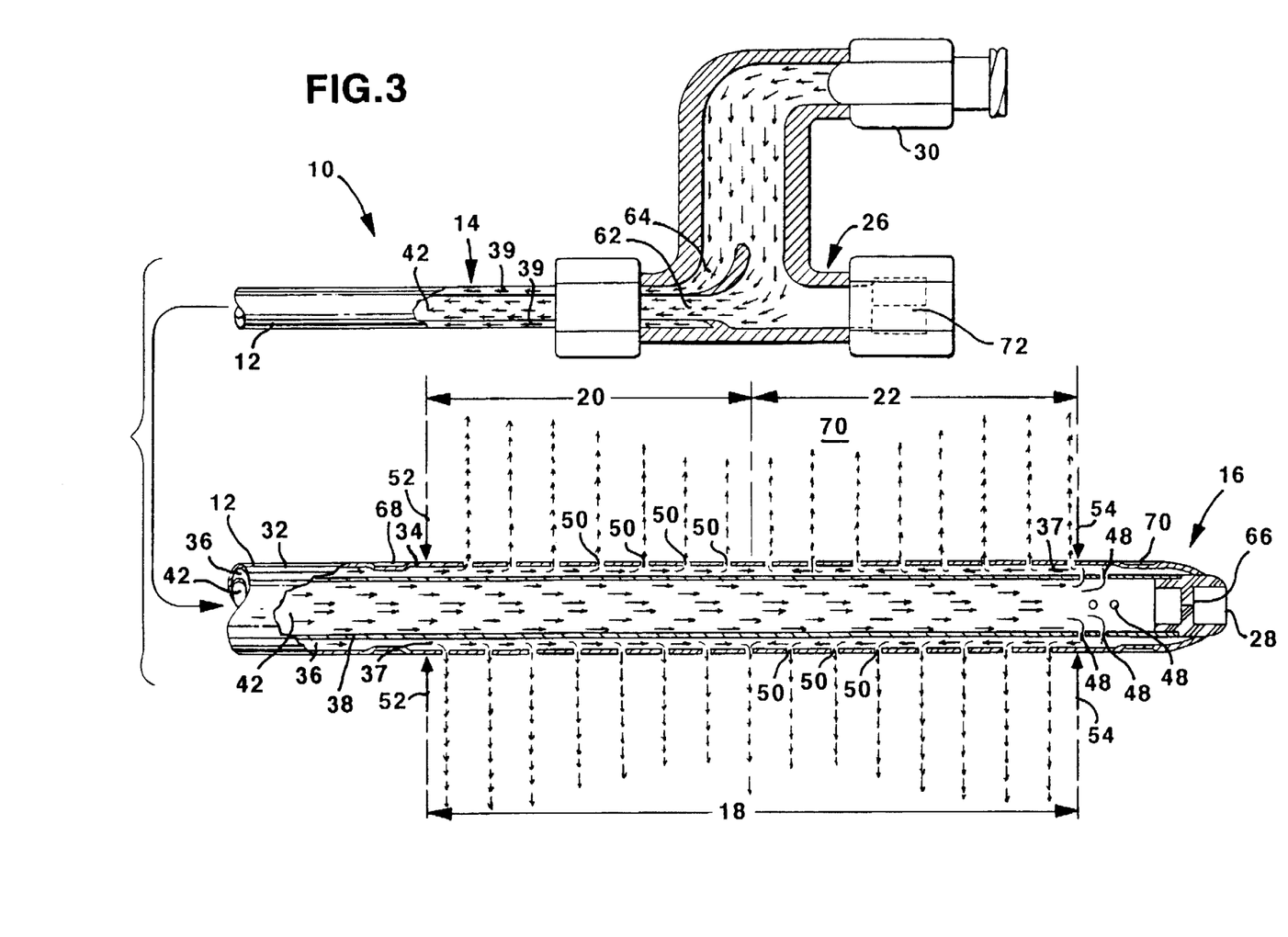
FIG. 3 is a cross-section view extending axially along the length of the infusion device of FIG. 1 illustrating the delivery of infusate through the first and second delivery lumens and the resulting infusate distribution profile along the length of the infusion segment in accordance with the first embodiment of the invention.

Turning to FIG. 3, it is a cross-section view extending axially along the length of the infusion device of FIG. 1 taken along lines 3–9 to 3–9 illustrating the delivery of infusate through first and second delivery paths, including the annular and inner lumens 36 and 42, and a resulting fixed infusate distribution profile 70 along the length of the infusion segment 18 in accordance with a first variation of the first embodiment of the invention. The infusate distribution profile 70 may be quantified or expressed in terms of flow rate through the side wall exit ports 50 or volume of infusate delivered therethrough over a given time period. In either case, the relative magnitude of delivered infusate is depicted by the lengths of the dotted lines of the infusate distribution profile 70 along the length of the infusion segment 18.

First and second fixed orifices 62 and 64, respectively, extending within proximal fitting 26 and side port 30, are in fluid communication with the first or inner infusion lumen 42 and the second infusion lumen 39 of the outer annular lumen 36. In FIG. 3, the first and second flow paths of the infusate are illustrated showing that the infusate delivered through the first delivery means flows in the first flow path distally through orifice 62 and the inner lumen 42, through the infusate transmission ports 48, through the distal manifold end opening 54 and proximally through the distal section of the annular lumen 36 constituting the infusate distribution manifold 37 and exiting the plurality of side hole exit ports 50, primarily those in the distal infusion section 22. The infusate delivered through the second delivery means is depicted flowing in the second flow path distally through the orifice 64, the proximal section of annular lumen 36, constituting the second infusion lumen 39 the proximal manifold end opening 52 and distally through the extension of annular lumen 36 constituting the infusate distribution manifold 37 and exiting the plurality of side wall exit ports 50, primarily those in the proximal infusion section 20. The considerations of the flow rate and fluid pressure of the infusate source coupled to the side fluid port 30, the lengths and cross-section areas of the infusion lumens 42 and 39, and the cross-section area of the fluid transmission ports 48 are taken into account in quantifying the flow resistance in the first and second flow paths terminating at the annular distal and proximal manifold end openings 54 and 52.

As a result, the infusate flows in first and second infusate flow rates through the distal and proximal manifold end openings 54 and 52 that are approximately the same, resulting in an infusate distribution profile 70 that is approximately symmetric in magnitude in the proximal and distal infusion sections 20 and 22. The infusate distribution profile 70 is relatively symmetric as shown in FIG. 3 with a fall-off in infusate delivery magnitude toward the junction of the proximal and distal sections 20 and 22 that depends on the overall length of the infusion segment 18.

Although it may not be necessary to do so, the resistances to infusate flow in the two flow paths may be taken into account in sizing the orifices 62 and 64 so that the first and second infusate flow rates through the distal and proximal manifold end openings 54 and 52, respectively, are relatively equal. To accomplish this, it may be necessary to make the size of the first orifice 62 greater in cross-section area than that of the second orifice 64.

Figure 6:
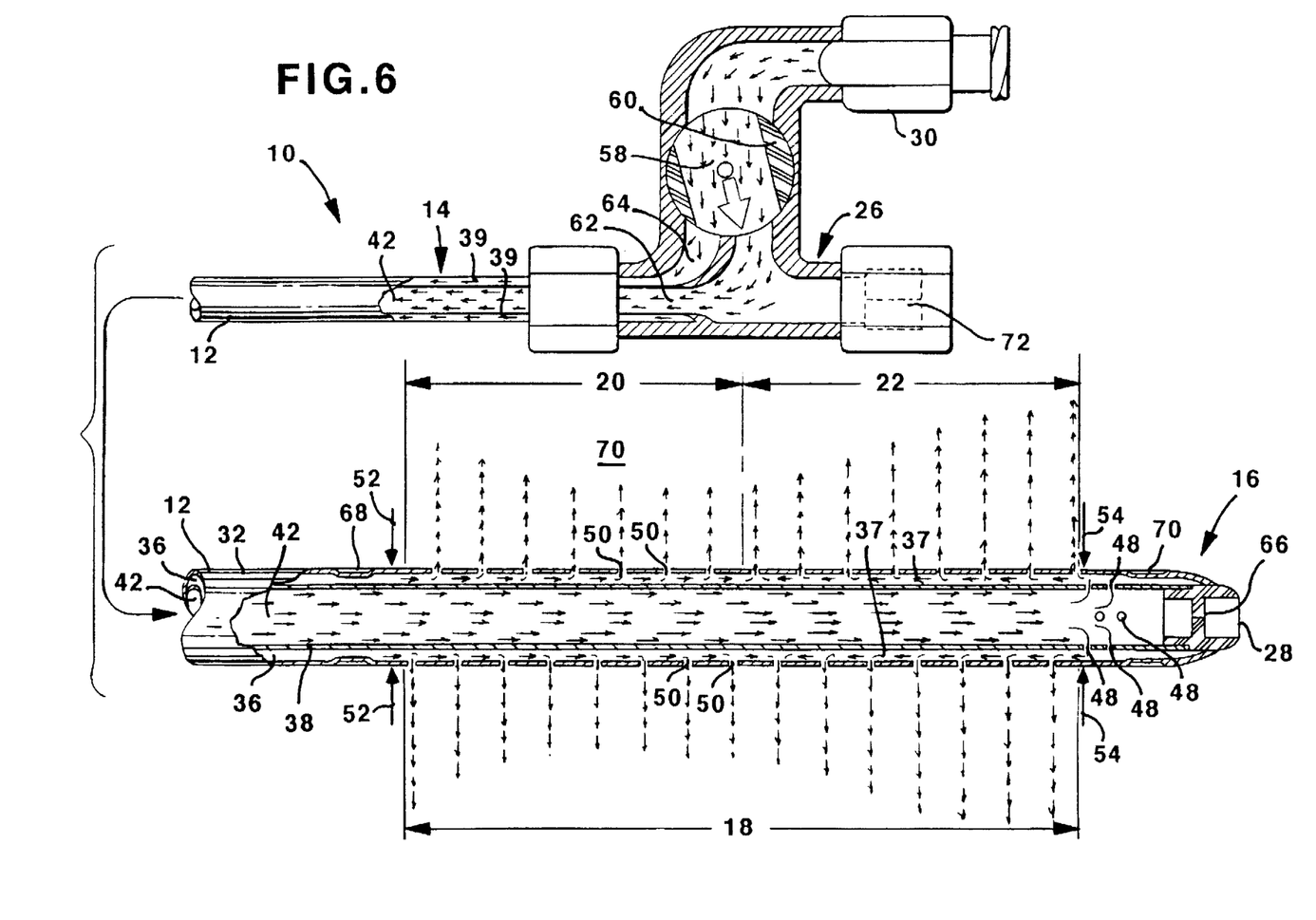
Figure 8:
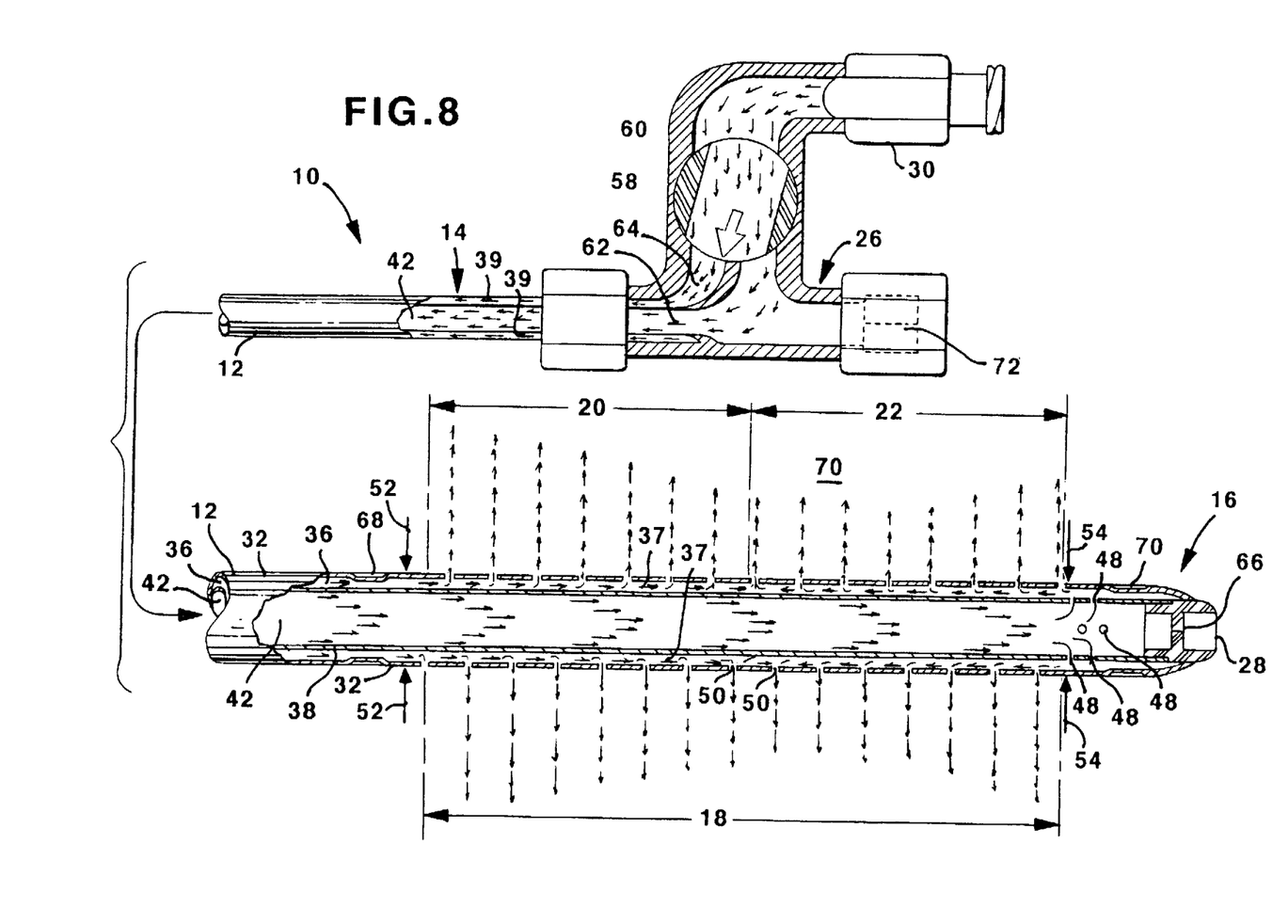

It is also possible in a second variation of the first embodiment to adjust the relative fixed sizes of the first and second orifices 62 and 64 or to otherwise adjust the first and second delivery means to intentionally create first and second infusate flow rates through the distal and proximal manifold end openings 54 and 52, respectively, that are not equal to one another to thereby bias the magnitude of the infusate distribution profile proximally or distally. The first and second orifices 62 and 64 may be sized in relation to the first and second flow resistances to establish a predetermined difference in the first and second flow rates, whereby infusate is delivered through the distal and proximal manifold end openings 54 and 52, respectively, at differing flow rates and fluid pressures for providing an asymmetric infusate distribution profile along the length of the infusion segment. FIGS. 6 and 8 illustrate examples of the infusate distribution profiles that may be achieved by such adjustments of the fixed sizes of the first and second orifices 62 and 64 or of the inner and annular lumens 42 and 36 or of the total cross-section area of the infusate transmission ports 48.

FIGS. 4–9 are cross-section views extending axially along the length of the infusion device 10 take along lines 3–9 to 3–9 of FIG. 1 illustrating the delivery of differing proportions of infusate through the first and second delivery means and the resulting infusate distribution profiles 70 along the length of the infusion segment 18. FIGS. 4–9 also show several positions of the flow diverting valve 60 that may be set in accordance with the second embodiment of the invention to tailor the infusate distribution profile 70 in a variety of ways. The flow diverting valve 60 may be formed as shown just proximal to the first and second orifices 62 and 64 in the infusate side port 30 and operated manually as the infusate diverting mechanism. The flow diverting valve 60 has a single channel 58 that can be oriented with respect to the first and second orifices 62 and 64 to effectively adjust their relative cross-section areas.

Figure 4:
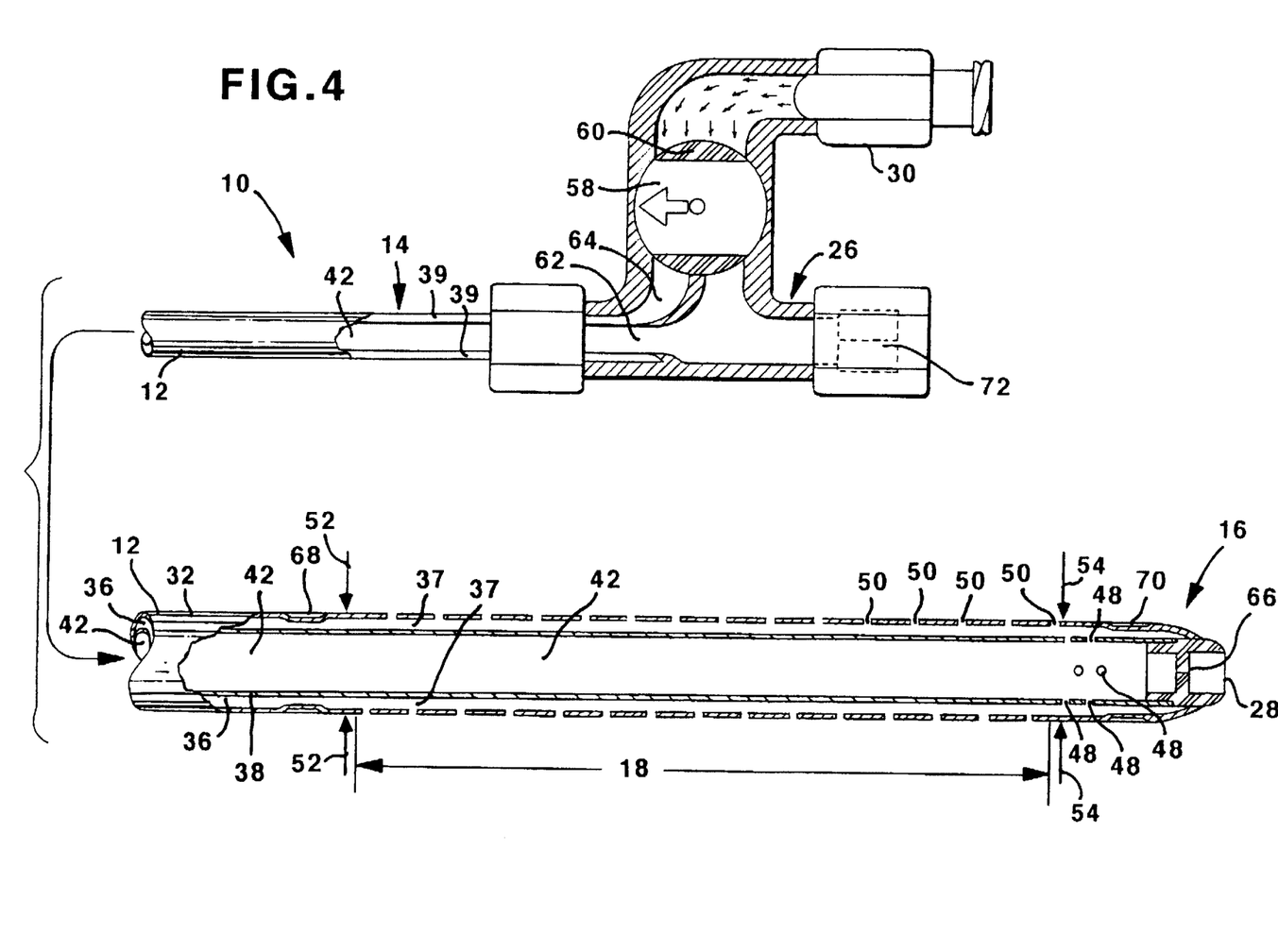
FIGS. 4–9 are cross-section views extending axially along the length of the infusion device of FIG. 1 illustrating the delivery of differing proportions of infusate through the first and second delivery lumens and the resulting infusate distribution profiles along the length of the infusion segment in accordance with the second embodiment of the invention

In FIG. 4, the flow diverting valve 60 is shown with channel 58 blocked, stopping any infusate delivery, which may be advantageous at times during the treatment of a patient when it is desired to temporarily stop delivery of the infusate. The closed valve position prevents backflow of blood from the patient's blood vessel out the infusate side port 30 during such a time period.

Figure 5:
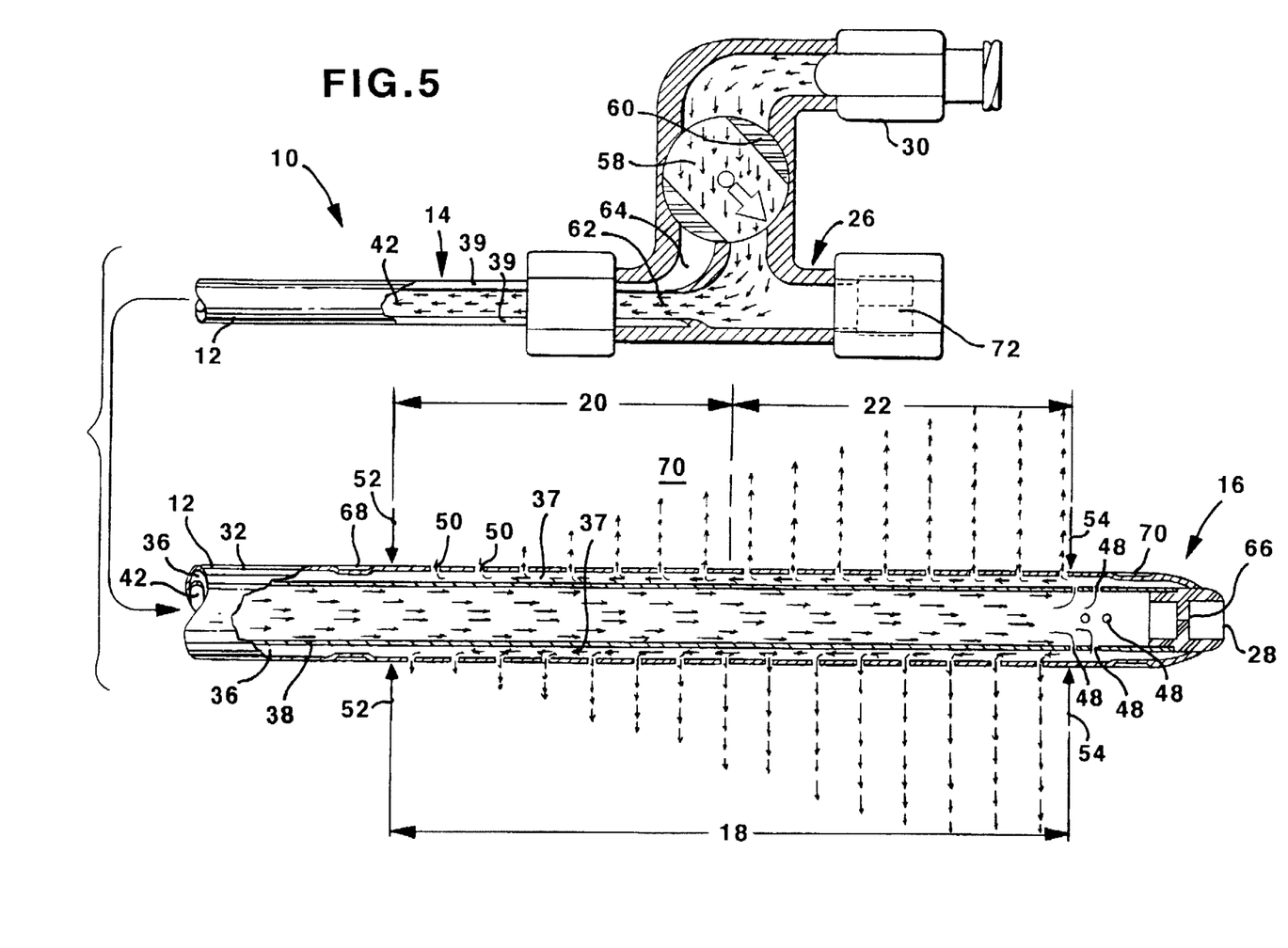

In FIG. 5, the flow diverting valve 60 is adjusted so that all of the infusate is delivered through channel 58 into first orifice 62 and the first delivery means and none is delivered through into second orifice 64. The resulting infusate distribution profile is biased toward the distal end 16 and falls off proximally through the infusion segment 18.

A shorter infusion length than the full length of infusion segment 18 may be selected if it is found desirable to do so either initially or during the course of delivery of the infusate in a given case.

In FIG. 6, the flow diverting valve 60 is adjusted so that channel 58 is aligned to restrict second orifice 64 while leaving first orifice 62 fully open. In this position, a greater proportion of the infusate is delivered through the first delivery means to the distal section 22 and a minor portion is delivered through the second delivery means, resulting in an infusate distribution profile still biased toward the distal end of the infusion segment 18 but with a greater amount of infusate delivered proximally along the infusion segment 18 than in the position of FIG. 5.

Figure 7:
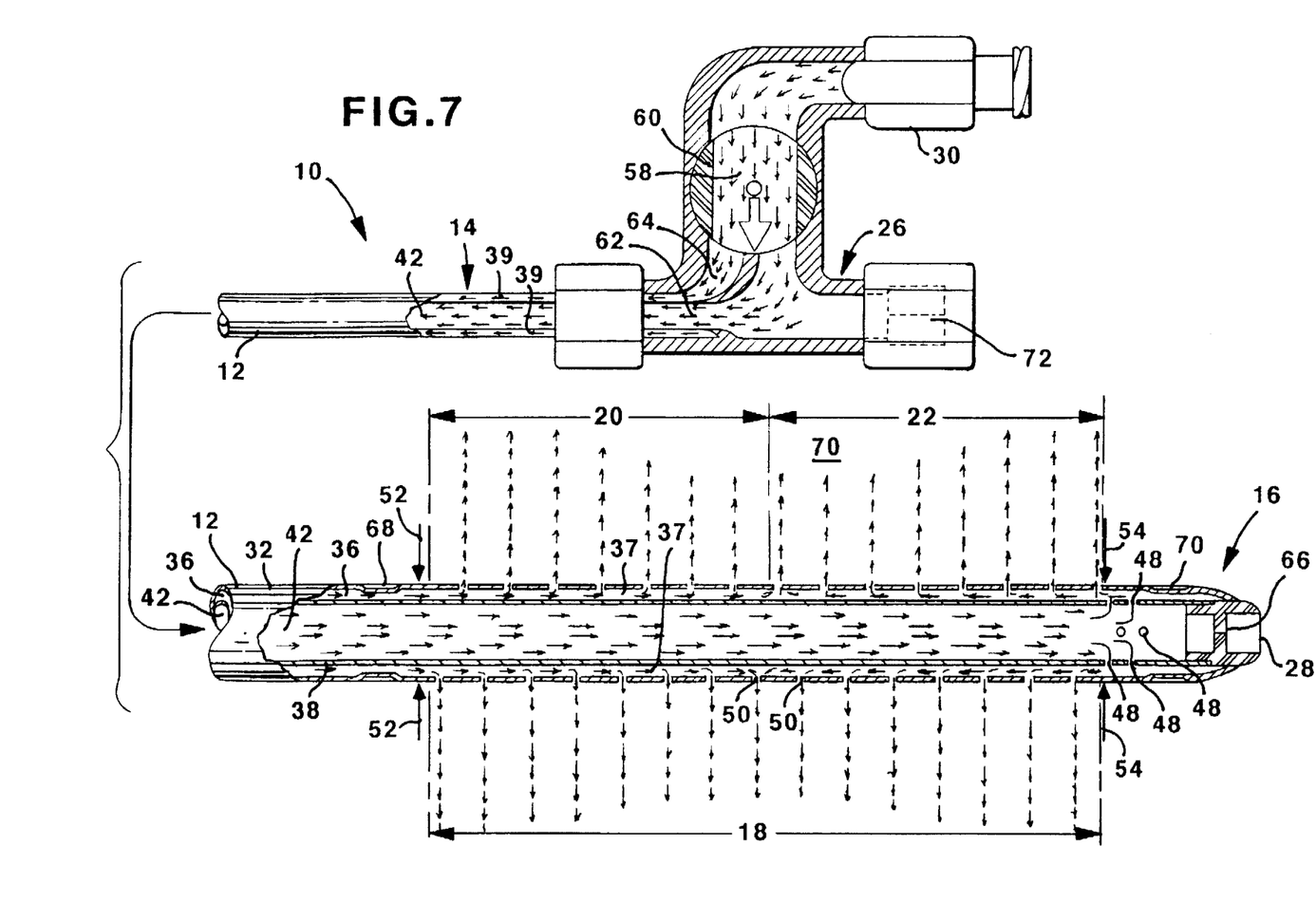

In FIG. 7, the flow diverting valve 60 is adjusted so that an equal proportion of the infusate is delivered through the first delivery means and the second delivery means resulting in the most symmetric infusate distribution profile 70 that can be attained along the infusion segment 18. Stated another way, the infusate is delivered at first and second flow rates through the distal and proximal manifold end openings 54 and 52, respectively, where the first and second flow rates are about equal to one another. The fall off in magnitude toward the center of infusion segment 18 is proportional to the length of the infusion segment 18.

To accomplish this, it is preferred that the sizings of the components of the tubular body 12 and first and second orifices 62 and 64 defining the first and second flow paths follow the teachings of the first variation of the first embodiment described above. However, to the extent that this may not be possible, the flow diverting valve 60 can be adjusted to a "neutral" position that compensates for any inherent differences in the first and second infusate flow rates, and the valve housing may be marked with the neutral position for achieving the symmetric infusate distribution profile.

In a situation where the infusate is delivered to dissolve an elongated blood clot, for example, and retrograde blood flow is present in the blood vessel or becomes present as infusate delivery becomes effective at restoring some degree of retrograde blood flow, it may be desirable to take advantage of the blood flow direction and concentrate the distribution of infusate distally so that it flows proximally. Initially, in a fully blocked vessel, the infusate may be distributed more uniformly in the proximal and distal sections 20 and 22 in the manner depicted in FIG. 7, then concentrated more distally in the manner of FIG. 6 before flow diverting valve 60 is adjusted to the position depicted in FIG. 5 as the retrograde blood flow increases.

In FIG. 8, the flow diverting valve 60 is adjusted so that a greater proportion of the infusate is delivered through the second delivery means to the proximal section 20 of the infusate segment 18 and a minor portion is delivered through the second delivery means to the distal section 22 of the infusion segment 18.

Figure 9:
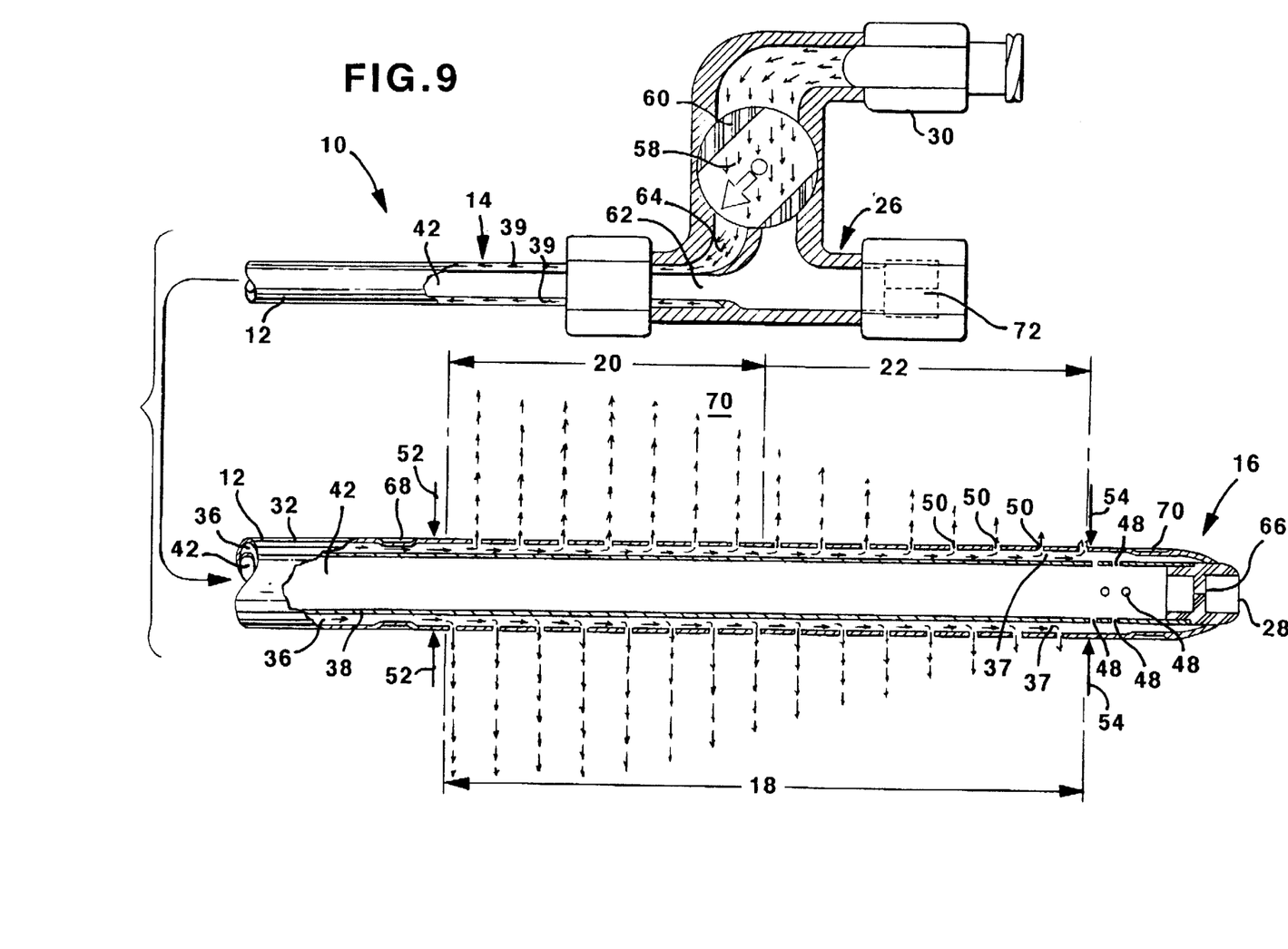

Finally, in FIG. 9, the flow diverting valve 60 is adjusted so that channel 58 is aligned with the second orifice 64 so that all of the infusate is delivered therethrough and none is delivered through the first orifice 62, resulting in an infusate distribution profile biased heavily within the proximal infusion section 20 and falling off distally through the distal infusion section 22 of infusion segment 18.

These positions of the flow diverting valve 60 and the resulting infusate distribution profiles 70 may also be used to shorten the length of the infusion segment 18 and concentrate the delivery of the infusate proximally either initially or as the infusate is delivered. In a situation where the infusate is delivered to dissolve a blood clot, for example, and where antegrade blood flow is present in the blood vessel or becomes present as infusate delivery becomes effective at restoring some degree of antegrade blood flow, it may be desirable to take advantage of the blood flow direction and concentrate the distribution of infusate proximally so that it flows distally. Initially, in a fully blocked vessel, the infusate may be distributed more uniformly in the proximal and distal infusion sections 20 and 22 in the manner depicted in FIG. 7, then concentrated more proximally in the manner of FIG. 8 before flow diverting valve 60 is adjusted to the position depicted in FIG. 9 as the antegrade blood flow increases.

As shown by the infusate distribution profiles of FIGS. 5-9, in any given patient procedure, an elongated blood clot may be treated with dissolving agent through the full infusion segment length, and as the clot is lysed in proximal or distal parts, the flow diverting valve 60 may be adjusted to shorten the effective infusion segment length and concentrate of the infusate where the clot remains. Also, the effective infusion segment length may be adjusted initially after the infusion segment is positioned in the blood vessel. Similar advantages may be taken advantage of in the delivery of diagnostic agents or other infusates.

In each of the embodiments of the invention, the proximal and distal ends of the infusion segment may be marked by providing radiopaque bands 68 and 70 around the outer tube 32 or the inner tube 38.

The preferred embodiment of the infusion device 10 includes a distal valve 66 that is penetrable by the guide wire 24 providing a fluid seal therebetween and is re-sealable upon removal of the guide wire 24. Other mechanisms known in the art may also be employed to selectively block the end opening 28 when the infusion device is introduced over the wire to the infusion site. As mentioned above, the infusion device 10 may also be used as an infusion wire having a removable core wire operating as a guide wire 24 substantially as described above for guiding advancement of the infusion wire through the obstruction or with a fixed core wire within the inner lumen 42 attached to the distal tip or with a core wire that abuts the distal tip but can be removed when the infusion wire is positioned in order to increase the inner lumen 42 cross-section area to achieve the desired infusate distribution profile.

While a substantially straight tubular member is depicted, it will be understood that it may be formed in the coiled wire configuration of the infusion device disclosed in the above-referenced '609 application.

While uniformly spaced apart and sized side wall exit ports 50 are contemplated, it will be understood that the size and concentration may be varied to adjust the total cross-section area of the side wall exit ports in any selected section of the outer tube 32 along the infusion segment 18. For example, a greater cross-section area may be effected toward the center of the infusion segment 18 to increase the magnitude of the infusate distribution profile centrally.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. An infusion device for delivering an infusate from an external source of infusate into a body lumen in an infusate distribution profile, said infusion device further comprising:

an elongated tubular body having an external side wall extending between a proximal tubular body end and a distal tubular body end adapted to be introduced intraluminally into a body lumen, said elongated tubular body formed of an elongated inner tube having an inner tube lumen and inner tube side wall and an elongated outer tube having an outer tube lumen and outer tube side wall arranged in a coaxial arrangement wherein said inner tube is located within said outer tube lumen and an annular lumen is thereby formed between the inner tube side wall and the outer tube side wall, said inner tube lumen having a proximal inner lumen end opening at said proximal tubular body end, and said annular tube lumen having a proximal annular lumen end opening at said proximal tubular body end;

an elongated infusion segment formed of a segment of said elongated tubular body adapted to be intraluminally positioned within the body lumen, said elongated infusion segment extending between a proximal infusion segment end and a distal infusion segment end and having a proximal infusion section extending distally from said proximal infusion segment end and a distal infusion section extending proximally from said distal infusion segment end;

an infusate distribution manifold formed of a segment of said annular lumen extending coextensively with said infusion segment, said infusate distribution manifold having a proximal distribution manifold end opening that allows flow of infusate into said infusate distribution manifold and then in a distal direction therethrough along said proximal infusion section of said infusion segment, and a distal distribution manifold end opening that allows flow of infusate into said infusate distribution manifold and then in a proximal direction therethrough along said distal infusion section of said infusion segment;

a plurality of side wall exit ports extending from said infusate distribution manifold through said outer tube side wall that allow flow of infusate from said infusate distribution manifold therethrough and into the body lumen, the individual side wall exit ports spaced apart along said outer tube side wall in said proximal and distal infusion sections of said infusion segment;

infusate transmission means formed in the distal end of said inner tube side wall for allowing transmission of infusate from the distal end of said inner tube lumen to said distal manifold end opening;

first infusate introduction means at said tubular body proximal end in fluid communication with said inner lumen proximal end opening for delivering infusate distally in a first flow path through said inner lumen and through said infusate introduction means and then through said distal manifold end opening at a first flow rate related to a first infusate flow resistance of the first flow path, such that infusate flows proximally through the infusate distribution manifold and primarily through the side wall exit ports in the distal infusion section and into the body lumen; and second infusate introduction means at said tubular body proximal end in fluid communication with said annular lumen proximal end opening for delivering infusate distally in a second flow path through a proximal segment of said annular lumen and through the proximal manifold end opening at a second flow rate related to a second infusate flow resistance of the second flow path such that infusate flows distally through the infusate distribution manifold and primarily through the side wall exit ports in the proximal infusion section and into the body lumen, whereby the first and second flow rates establish the infusate distribution profile of infusate flowing through the plurality of side wall exit ports along the infusion segment.

2. The infusion device of claim 1 wherein:

said first infusate introduction means further comprises a first fixed orifice coupled between said source of infusate and said inner lumen proximal end opening sized as a function of said first infusate flow resistance for adjusting said first flow rate into said distal manifold end opening; and said second infusate introduction means further comprises a second fixed orifice coupled between said source of infusate and said annular lumen proximal end opening sized as a function of said second infusate flow resistance for adjusting said second flow rate into said distal manifold end opening.

3. The infusion device of claim 2 wherein:

said first and second orifices are sized to compensate for any difference in said first and second flow rates in said first and second paths, whereby infusate is delivered through said distal and proximal manifold end openings, respectively, at approximately the same flow rate and fluid pressure for providing a symmetric infusate distribution profile along the length of said infusion segment.

4. The infusion device of claim 2 wherein:

said first and second orifices are sized in relation to said first and second flow resistances to establish a predetermined difference in said first and second flow rates, whereby infusate is delivered through said distal and proximal manifold end openings, respectively, at differing flow rates and fluid pressures for providing an asymmetric infusate distribution profile along the length of said infusion segment.

5. The infusion device of claim 4 wherein said first and second orifices are sized such that said first flow rate exceeds said second flow rate, resulting in an infusate distribution profile exhibiting a greater magnitude along said distal portion of the infusion segment than along said proximal portion of the infusion segment.

6. The infusion device of claim 4 wherein said first and second orifices are sized such that said second flow rate exceeds said first flow rate, resulting in an infusate distribution profile exhibiting a greater magnitude along said proximal portion of the infusion segment than along said distal portion of the infusion segment.

7. The infusion device of claim 1 wherein said first and second infusate introduction means further comprise an adjustable valve mechanism coupled to said source of infusate to receive the infusate and coupled to said inner and annular lumen proximal end openings for proportionally diverting the infusate therethrough in adjustable proportions resulting in said first and second flow rates.

8. The infusion device of claim 7 wherein said adjustable valve mechanism further comprises a flow diverting valve that may be selectively adjusted in use to define the relative sizes of a first orifice coupled to said inner lumen proximal end opening for determining said first flow rate through said distal manifold end opening and a second orifice coupled to said annular lumen proximal end opening for determining said second flow rate through said proximal manifold end opening.

9. The infusion device of claim 8 wherein said flow diverting valve is adjustable to size said first and second orifices in relation to one another for delivering infusate through said distal and proximal manifold end openings, respectively, at approximately the same flow rate and fluid pressure for providing a symmetric infusate distribution profile along the length of said infusion segment.

10. The infusion device of claim 8 wherein said flow diverting valve is adjustable to size said first and second orifices in relation to one another for delivering infusate through said distal and proximal manifold end openings, respectively, at differing flow rates and fluid pressures for providing an asymmetric infusate distribution profile along the length of said infusion segment.

11. The infusion device of claim 10 wherein said flow diverting valve is adjustable to size said first orifice to be larger than said second orifice, whereby said first flow rate exceeds said second flow rate, resulting in an infusate distribution profile exhibiting a greater magnitude along said distal portion of the infusion segment than along said proximal portion of the infusion segment.

12. The infusion device of claim 10 wherein said flow diverting valve is adjustable to size said second orifice to be larger than said first fixed orifice, whereby second flow rate exceeds said first flow rate, resulting in an infusate distribution profile exhibiting a greater magnitude along said proximal portion of the infusion segment than along said distal portion of the infusion segment.

13. The infusion device of claim 1 wherein said first and second infusate introduction means are adjustable to provide approximately the same first and second flow rates, resulting in an infusate distribution profile that is approximately symmetric in magnitude between said proximal and distal infusion segment ends.

14. The infusion device of claim 13 wherein said infusate distribution profile exhibits a higher magnitude adjacent said proximal and distal infusion segment ends than in a central region of said infusion segment.

15. The infusion device of claim 1 wherein said first and second means are adjustable to provide differing first and second flow rates, resulting in an infusate distribution profile that is asymmetric along the length of the infusion segment.

16. The infusion device of claim 15 wherein said first flow rate exceeds said second flow rate, resulting in an infusate distribution profile exhibiting a greater magnitude along the distal infusion section than along the proximal infusion section.

17. The infusion device of claim 15 wherein said second flow rate exceeds said first flow rate, resulting in an infusate distribution profile exhibiting a greater magnitude along the proximal infusion section than along the distal infusion section.

18. An infusion device for delivering an infusate from an external source of infusate into a body lumen comprising:

an elongated tubular body having a proximal tubular body end and a distal tubular body end formed of an outer tube with an outer tube side wall that extends between said proximal tubular body end and said distal tubular body end;

an elongated infusion segment adapted to be intraluminally positioned within a corresponding length of the body lumen extending along said elongated tubular body, said infusion segment having a proximal infusion section and a distal infusion section;

an infusate distribution manifold formed within said outer tube extending coextensively along said infusion segment, said infusate distribution manifold having a proximal distribution manifold end opening that allows flow of infusate into said infusate distribution manifold and then in a distal direction therethrough along said proximal infusion section of said infusion segment, and a distal distribution manifold end opening that allows flow of infusate into said infusate distribution manifold and then in a proximal direction therethrough along said distal infusion section of said infusion segment;

a plurality of side wall exit ports extending through the outer tube side wall into said infusate distribution manifold that allow flow of infusate from said infusate distribution manifold therethrough and into the body lumen, the individual side wall exit ports spaced apart along said outer tube side wall in said proximal and distal infusion sections of said infusion segment;

first delivery means extending through said tubular body from said proximal tubular body end to said distal distribution manifold end opening for receiving infusate from said external source and for delivering infusate distally within said tubular body and through said distal distribution manifold end opening at a first flow rate such that infusate flows distally through said first delivery means and said distal distribution manifold end opening and then flows proximally through said infusate distribution manifold and primarily through the side wall exit ports distributed along said outer tube side wall in said distal infusion section and into the body lumen;

second delivery means extending through said tubular body from said proximal tubular body end to said proximal distribution manifold end opening separated from said first delivery means extending through said tubular body for receiving infusate from said external source and for delivering infusate distally within said tubular body and through said proximal distribution manifold end opening at a second flow rate such that infusate flows distally through said second infusion lumen, said proximal distribution manifold end opening and then distally through said infusate distribution manifold and primarily through the side wall exit ports distributed along said outer tube side wall in said proximal infusion section and into the body lumen; and infusate introduction means for delivering the infusate from said external source of infusate into said first and second delivery means at said proximal tubular body end whereby infusate is delivered through said plurality of side wall exit ports of said infusion segment and into the body lumen in a predetermined flow profile.

19. The infusion device of claim 18 wherein:

said first delivery means further comprises a first infusion lumen extending through said tubular body from said proximal tubular body end to said distal distribution manifold end opening; and said second delivery means further comprises a second infusion lumen extending through said tubular body from said proximal tubular body end to said proximal distribution manifold end opening separated from said first infusion lumen extending through said tubular body.

20. The infusion device of claim 19 wherein said infusate introduction means further comprises a proximal fitting attached to said proximal tubular body end which is attached to said source of infusate to receive infusate; and said proximal fitting further comprises:

first orifice means coupled to a proximal end opening of said first infusion lumen for delivering infusate in said proximal fitting at said first flow rate into said distal manifold end opening, and second orifice means coupled to a proximal end opening of said second infusion lumen for delivering infusate in said proximal fitting at said second flow rate into said proximal manifold end opening.

21. The infusion device of claim 20 wherein said first and second orifice means further comprise first and second fixed size orifices, respectively, sized with relation to one another and to the sizes of said first and second infusion lumens, respectively, for delivering infusate through said distal and proximal manifold end openings, respectively, at approximately the same flow rate and fluid pressure for providing a symmetric infusate distribution profile of the amount of infusate delivered through side wall exit ports along the length of said infusion segment.

22. The infusion device of claim 20 wherein said first and second orifice means further comprise first and second fixed size orifices, respectively, sized with relation to one another and said first and second infusion lumens, respectively, for delivering infusate through said distal and proximal manifold end openings, respectively, at differing first and second flow rates and fluid pressures for providing an asymmetric infusate distribution profile of the amount of infusate delivered through side wall exit ports along the length of said infusion segment.

23. The infusion device of claim 22 wherein said first fixed orifice is sized to be larger than said second fixed orifice, whereby said first flow rate exceeds said second flow rate, resulting in an infusate distribution profile exhibiting a greater amount of infusate delivered through side wall exit ports along said distal section of said infusion segment than the amount of infusate delivered through side wall exit ports along said proximal section of said infusion segment.

24. The infusion device of claim 22 wherein said second fixed size orifice is sized to be larger than said first fixed size orifice, whereby said second flow rate exceeds said first flow rate, resulting in an infusate distribution profile exhibiting a greater amount of infusate delivered through side wall exit ports along said proximal section of said infusion segment than the amount of infusate delivered through side wall exit ports along said distal section of said infusion segment.

25. The infusion device of claim 19 wherein said infusate introduction means further comprises flow rate controlling means adjusting the first and second flow rates with respect to one another to vary the infusate distribution profile of infusate flowing through the plurality of side wall exit ports in said proximal and distal infusion sections.

26. The infusion device of claim 25 wherein said flow rate controlling means further comprises an adjustable valve mechanism coupled to said source of infusate to receive the infusate and coupled to said first and second infusion lumens for directing the infusate into said first and second infusion lumens in adjustable proportions resulting in said first and second flow rates.

27. The infusion device of claim 26 wherein said adjustable valve mechanism further comprises a flow diverting valve having a channel that may be selectively adjusted in use to define the relative sizes of a first orifice coupled to the first infusion lumen for determining said first flow rate through said distal manifold end opening and a second orifice coupled to said second infusion lumen for determining said second flow rate through said proximal manifold end opening.

28. The infusion device of claim 27 wherein said channel of said flow diverting valve is adjustable to size said first and second orifices in relation to one another and with said first and second infusion lumens, respectively, for delivering infusate through said distal and proximal manifold end openings, respectively, at approximately the same flow rate and fluid pressure for providing a symmetric infusate distribution profile in the amount of infusate delivered through side wall exit ports along the length of said infusion segment.

29. The infusion device of claim 27 wherein said channel of said flow diverting valve is adjustable to size said first and second orifices in relation to one another and with said first and second infusion lumens, respectively, for delivering infusate through said distal and proximal manifold end openings, respectively, at differing first and second flow rates and fluid pressures for providing an asymmetric infusate distribution profile in the amount of infusate delivered through side wall exit ports along the length of said infusion segment.

30. The infusion device of claim 29 wherein said first orifice is sized to be larger than said second orifice through adjustment of said channel of said flow diverting valve, whereby said first flow rate exceeds said second flow rate, resulting in an infusate distribution profile exhibiting a greater amount of infusate delivered through side wall exit ports along said distal section of said infusion segment than the amount of infusate delivered through side wall exit ports along said proximal section of said infusion segment.

31. The infusion device of claim 29 wherein said second orifice is sized to be larger than said first orifice through adjustment of said channel of said flow diverting valve, whereby said second flow rate exceeds said first flow rate, resulting in an infusate distribution profile exhibiting a greater amount of infusate delivered through side wall exit ports along said proximal section of said infusion segment than the amount of infusate delivered through side wall exit ports along said distal section said infusion segment.

32. The infusion device of claim 19 wherein said infusate introduction means further comprises:

first means coupled to the first infusion lumen for delivering the infusate at said first flow rate through said distal manifold end opening; and second means coupled to the second infusion lumen for delivering the infusate at said second flow rate through said proximal manifold end opening.

33. The infusion device of claim 18 wherein said first and second flow rates are approximately the same, resulting in an infusate distribution profile of infusate delivered through side wall exit ports extending along said infusion segment that is approximately symmetric in magnitude between said proximal and distal infusion sections.

34. The infusion device of claim 33 wherein said infusate distribution profile exhibits a higher amount of infusate delivered through side wall exit ports adjacent said proximal and distal infusion segment ends than the amount of infusate delivered through side wall exit ports in a central region of said infusion segment.

35. The infusion device of claim 18 wherein said first and second flow rates differ, resulting in an infusate distribution profile of infusate delivered through side wall exit ports that is asymmetric along the length of said infusion segment.

36. The infusion device of claim 18 wherein said first flow rate exceeds said second flow rate, resulting in an infusate distribution profile exhibiting a greater amount of infusate delivered through side wall exit ports along the distal infusion section than the amount of infusate delivered through side wall exit ports along the proximal infusion section of said infusion segment.

37. The infusion device of claim 18 wherein said second flow rate exceeds said first flow rate, resulting in an infusate distribution profile exhibiting a greater amount of infusate delivered through side wall exit ports along said proximal infusion section than the amount of infusate delivered through side wall exit ports along said distal infusion section.

* * * * *